United States Patent [19]

Armstrong, III et al.

[11] Patent Number: 5,508,435
[45] Date of Patent: Apr. 16, 1996

[54] ASYMMETRIC HYDROGENATION OF BETA- OR GAMMA-KETOESTERS AND BETA- OR GAMMA-KETOAMIDES

[75] Inventors: Joseph D. Armstrong, III, Westfield; Lisa DiMichele, Plainfield; Alan W. Douglas, Monmouth Junction; Jennifer L. Keller, Princeton; Steven A. King, Summit; Andrew S. Thompson, Mountainside; Thomas R. Verhoeven, Cranford, all of N.J.

[73] Assignee: Merck & Co., Inc., Rahway, N.J.

[21] Appl. No.: 177,481

[22] Filed: Jan. 5, 1994

Related U.S. Application Data

[63] Continuation-in-part of Ser. No. 922,355, Jul. 13, 1992.

[51] Int. Cl.$^6$ .............. C07D 313/02; C07D 207/24; C07D 211/40; C07D 225/02; C07C 223/04
[52] U.S. Cl. .............. 548/543; 548/482; 546/216; 549/346; 549/356; 549/429; 560/115; 560/151; 560/179; 564/186; 435/6; 540/524; 540/531
[58] Field of Search ................... 548/543, 482; 546/216; 549/346, 356, 429; 560/115, 157, 179

[56] References Cited

U.S. PATENT DOCUMENTS 4,933,482   6/1990   Sayo et al. ........................... 558/252

FOREIGN PATENT DOCUMENTS 0295109   of 0000   European Pat. Off. .
0484271   of 0000   European Pat. Off. .
53-105421 of 0000   Japan .

OTHER PUBLICATIONS

Noyori, et al., Acc. Chem. Res., vol. 23, pp. 345–350 (1990).
Kitamura, et al., Tetrahedron Letters, vol. 32(33), pp. 4163–4166 (1991).
Taber, et al., Tetrahedron Letters, vol. 32(34), pp. 4227–4230 (1991).
Keck and Murry, J. Org. Chem. vol. 56, pp. 6606–6611 (1991).
Noyori, et al. J. Am. Chem. Soc. vol. 109, pp. 5856–5858 (1987).
Jones, et al., J. Org. Chem. vol. 54, pp. 17–19 (1989).
Kitamura, et al., Tetrahedron Letters, vol. 29, No. 13, pp. 1555–1556 (1988).
Nishi, et al., Tetrahedron Letters, vol. 29, No. 48, pp. 6327–6330 (1988).
Schreiber, et al, J. Am. Chem. Soc., vol. 110, No. 18, pp. 6210–6218 (1988).
Ikariya, et al., J. Chem. Soc., Chem Commun., pp. 922–924 (1985).
Gamage, et al., J. Chem. Soc., Chem. Commun., pp. 894–895 (1987).
Joshi, et al., Inorg. Chimica Acta, 198–200, pp. 283–296 (1992).
Ohkuma et al., Tet. Ltrs, vol. 31, No. 38, pp. 5509–5512 (1990).
Joshi and James, J. Chem. Soc., Chem. Commun., pp. 1785–1786 (1989).
Taber, et al., J. Org. Chem., vol. 57, pp. 5990–5994 (1992).
Taber, et al., J. Am. Chem. Soc., vol. 113, pp. 6639–6645 (1991).
James, et al., J. Molecular Catalysis, vol. 41, pp. 147–161 (1987).
Kitamura, et al., Org Syn., vol. 71, pp. 1–13 (1992).
Hampton, et al., Inorg. Chem., vol. 31, pp. 5509–5520 (1992).
Ohta, et al., Inorg. Chem., vol. 27, pp. 566–569 (1988).
Dekleva, et al., Inorg. Chimica Acta, vol. 100, pp. 49–56 (1985).
Thorburn, et al., Inorg. Chem., vol. 25, pp. 234–240 (1986).
James, et al., Inorg. Chimica Acta, vol. 29, pp. L237–L238 (1978).
Mudalige, et al., J. Chem. Soc., Chem. Commun., pp. 830–832 (1993).
Mashima, et al., J. Chem. Soc., Chem Commun. No. 9, pp. 609–610 (1991).
Ohta et al., Tet Ltrs, vol. 33, No. 5, pp. 635–638 (1992).
Mashima, et al., J. Chem. Soc., Chem. Commn., pp. 1208–1210 (1989).
Ohta, et al., Tet. Ltrs, vol. 31, No. 49, pp. 7189–7192 (1990).
Takasago Int'l Corp., Asymmetric Synthesis: Asymmetric Hydrogenation Using BINAP—Complex Catalysts.
Hampton, et al., Inorg. Chimica Acta, vol. 145, pp. 165–166 (1988).
Cotton and Wilkinson, Advance Inorganic Chemistry, 5 Edition, "Chemistry of the Transition Elements", pp. 878–900 (1988) Wiley Inter. Sci.
Noyori, Chemtech, pp. 360–367 (Jun. 1992).
Kitamura, et al., J. Am. Chem. Soc., vol. 110, pp. 629–631 (1988).

*Primary Examiner*—David B. Springer
*Attorney, Agent, or Firm*—Valerie J. Camara; Mark R. Daniel; Joseph F. DiPrima

[57] ABSTRACT

β- or γ-Ketoesters and β- or γ-ketoamides are asymmetrically reduced with a Ru(II)-BINAP derived catalyst at about 40° C. and about 50N/mm$^2$ of hydrogen in the presence of a strong acid.

18 Claims, 2 Drawing Sheets

ASYMMETRIC HYDROGENATION OF BETA- OR GAMMA-KETOESTERS AND BETA- OR GAMMA-KETOAMIDES

This is a continuation in part of application Ser. No. 07/922,355 filed Jul. 13, 1992, abandoned.

SUMMARY OF THE INVENTION

The present invention relates to a novel process in which it has been shown that in the presence of trace amounts of strong acid an asymmetric hydrogenation proceeds at low temperatures and readily attainable pressures with substrate/catalyst ratios up to about 10,000. The reaction can be carried out at pressures of less than or equal to 150 psi as such the reaction does not require special equipment to run the reaction and can be carried out on a pilot plant scale.

Another aspect of this invention is a simple reproducible procedure for preparation of purified catalyst. This invention also relates to the identification of the catalyst responsible for carrying out this process.

BACKGROUND OF THE INVENTION

Asymmetric hydrogenation using the Ru(II)-BINAP or Ru(II)-t-BINAP system (ruthenium complexes of 2,2'-bis-(diphenylphosphino)-1,1'-binaphthyl or 2,2'-bis(di-p-tolylphosphino)-1,1'-binaphthyl) introduced by Noyori, et al. provides high enantioselectivity over a wide range of substrates with remarkable turnover (Noyori et al. *Acc, Chem, Res.*, 23, 345 (1990)). However, all reports concerning the reduction of 13-ketoesters (Noyori et al., *J. Am. Chem. Soc.* 109, 5856 (1987)) suffer from the need for temperatures greater than 80° C. or hydrogen pressures greater than 6895 N/mm$^2$ where special apparatus is required (Kitamura et al., *Tetrahedron Lett.*, 32, 4163 (1991); Taber et al, *Tetrahedron Lett.*, 32, 4227 (1991); Keck et al, *J. Org. Chem.*, 56, 6606(1991)).

BRIEF DESCRIPTION OF THE FIGURES

FIG. 2. Expansion of the 3.0 ppm to 3.5 ppm region of 400.13 MHz $^1$H NMR of [(C$_2$H$_5$)$_2$NH$_2$]$^+$[Ru$_2$Cl$_5$((R)-BINAP)$_2$]$^-$•CH$_3$Ph in CD$_2$Cl$_2$ at −40° C. (a) is the fully coupled spectrum of this region; (b) is the decoupled spectrum of this region resulting from the irradiation of the peak at 8.53 ppm; and (c) is the decoupled spectrum of this region resulting from the irradiation of the peak at 1.41 ppm.

DETAILED DESCRIPTION OF THE INVENTION

The novel process for the asymmetric reduction of β- or γ-ketoesters and β- or γ-ketoamides comprises adding a chiral ruthenium BINAP or t-BINAP catalyst, for example [(C$_2$H$_5$)$_2$NH$_2$]$^+$[Ru$_2$Cl$_5$[(S) -BINAP]$_2$]$^-$, [(C$_2$H$_5$)$_2$NH$_2$]$^+$[Ru$_2$Cl$_5$[(S)-t-BINAP]$_2$]$^-$, [RuCl(PhH)(BINAP)]Cl or [RuCl(PhH)(t-BINAP)]Cl catalyst to a solution of the β- or γ-ketoesters and β- or γ-ketoamides in a C$_{1-3}$ alkanol, preferably methanol, followed by the addition of a strong acid and reducing the β-or γ-ketoesters and β-or γ-ketoamides by agitation in the presence of hydrogen.

wherein:

R$^1$ is straight or branched C$_1$–C$_4$ alkyl;

X is O or NR$^5$;

Y is C(R$^2$)$_2$ or a single bond;

R$^2$ is: H, or straight or branched C$_1$–C$_6$ alkyl;

R$^3$ is: H, straight or branched C$_1$–C$_6$ alkyl, CH$_2$NHCOR$^6$, or R$^1$ and R$^3$ taken together form a 5 to 7 membered lactone or lactam;

R$^4$ is:

CH$_3$, (a)

CH$_2$Cl, (b)

(c)

(d)

(e)

(f)

(g)

(h)

(i)

(j)

or

CH$_2$CH$_2$CH$_2$OCH$_3$; (k)

R$^3$ and R$^4$ taken together form a ring of 5 to 7 carbons, in which R$^3$ and R$^4$ represent a carbon chain of 3 to 5 carbons;

R$^5$ is H, straight or branched C$_1$–C$_4$ alkyl, or CO$_2$ C$_1$–C$_4$ alkyl; and $R^6$ is straight or branched $C_1$–$C_4$ alkyl, or O—$C_1$–$C_4$ alkyl, phenyl, O-benzyl.

| Abbreviations | |
|---|---|
| BINAP | 2,2'-bis(diphenylphosphino)-1,1'-binaphthyl |
| t-BINAP | 2,2'-bis(di-p-tolylphosphino)-1,1'-binaphthyl |
| arBINAP | in the instant application represents all chiral ligands of 2,2'-bis(diarylphosphino)-1,1'-binaphthyl The term aryl is defined as phenyl, o-, m-, or p-tolyl. It is understood that although the specific stereochemistry is not recited that the ligand utilized is either the R- or the S-antipode. The selection of the R- or the S-arBINAP ligand will determine the stereochemistry of the β- or γ-hydroxyesters and β- or γ-hydroxyamides produced. |
| * | The asterik is being used to represent a specific enantiomer which is dependent on the stereochemistry of the BINAP employed. |
| 1 N/mm$^2$ | is equivalent to approximately 0.145 psi |
| Boc | t-butyloxycarbonyloxy |
| Ms | methanesulfonyl |
| COD | Cyclooctadienyl |
| om | overlapping multiplet |

The amount of catalyst relative to amount of substrate over about 0.02 mole % is not critical, and excess catalyst will not seriously effect yield and enantiomeric purity, but amounts up to about 0.1 mole % are quite adequate.

The concentration of substrate in the alkanol is preferably about 0.5 to about 2.25M although the concentration is not critical. It is preferred that the alkanol solvent be deoxygenated before reduction such as by flowing nitrogen for several minutes.

The strong acid used in the novel process is about 0.1 to 10 mole % of HCl, $H_2SO_4$, $H_3PO_4$, $CH_3SO_3H$, or the like, preferably HCl, $H_2SO_4$, or $CH_3SO_3H$.

The reaction mixture is agitated by shaking or stirring and the reduction is accomplished at about 40°–50° C. and a hydrogen pressure of about 50 to about 1400 N/mm$^2$ until the required hydrogen uptake has occurred, usually in about 3–8 hours. Under the above-described conditions an enantiomeric excess >97% is routinely achieved for an achiral starting β or γ-ketoester and β or γ-ketoamide and the reaction is diastereoselective when the starting β- or γ-ketoester and β- or γ-ketoamide is chiral.

There is a dramatic dependence of the reaction on low levels of strong acid A reaction mixture of a β- or γ-ketoester, or a β- or γ-ketoamide and catalyst, containing no acid, was exposed at 345 N/mm$^2$ (50 psi) of hydrogen at 50° C. for 24 hours with no hydrogen uptake. When 1 mole % HCl was added, the reaction went to completion in 3 hours. Sulfuric acid was equally effective. Significantly, the catalyst [RuCl(PhH)((R)-BINAP)]Cl, which contains no endogenous amine, also shows this acid dependence. A very low concentration of acid after neutralization of any basic impurities is required for maximum reaction rate. Any further increase in acid concentration provides no rate enhancement.

The catalyst is easily prepared using standard anaerobic techniques from commercially available (cyclooctadiene)ruthenium dichloride. Filtration of the product using a double ended filter provides a pure product, $[(C_2H_5)_2NH_2]^+$ $[Ru_2Cl_5(BINAP)_2]^-$ as a solvate, such as, benzene, toluene, xylene, chlorobenzene, or 1,2-, 1,3-, or 1,4-dichlorobenzene, etc.

Asymmetric reduction of a β-ketoester to the corresponding enantiomerically pure β-hydroxyester is an important synthetic step in the synthesis of a number of important useful chemical products such as:

1. The immunosuppressive agent, FK-506 (Jones et al. *J. Org. Chem.*, 54, 17–19 (1989));
2. Colletal (Keck et al., *J. Org. Chem.*, 56, 6606–6611 (1991));
3. Carnitine (*Tetrahedron Letters*, 29, 1555–1556 (1988));
4. Statine (Nishi et al., *Tetrahedron Letters*, 29, 6327–6330 (1988):
5. Gleosporine (Schreiber et al., *J. Amer. Chem. Soc.*, 110, 6210–6218 (1988)).

Another important type of product involving an asymmetric reduction of a β-ketoester in its synthesis is a group of carbonic anhydrase inhibitors which are topically effective in the treatment of ocular hypertension and glaucoma associated therewith. This class of compounds has the general structure:

or a pharmaceutically acceptable salt thereof, wherein R is $C_{1-5}$ alkyl; and $R^1$ is hydrogen, $C_{1-3}$ alkyl or $C_{1-3}$ alkoxy-$C_{1-3}$ alkyl and are disclosed in U.S. Pat. No. 4,797,413, issued Jan. 10, 1989. The series of steps in the synthesis depicted below for the topical carbonic anhydrase inhibitor, wherein R is defined as n-propyl and R' is defined as methoxypropyl, is representative of the process of this invention.

-continued

The novel process of this invention is depicted as 2→3 in the above reaction scheme. The enantiomerically pure alcohol produced in this step is responsible for installing the optical activity of the carbonic anhydrase inhibitors. Its activation and displacement with inversion provides the optically pure 5 which can be cyclized to the key intermediate 6 which contains the carbon skeleton of these compounds.

The following examples further illustrate the use of the process for the preparation of the compounds of Formula I and the use of this catalyst in this process and, as such, are not be considered or construed as limiting the invention recited in the appended claims.

EXAMPLE 1

Catalyst Preparation (BINAP)

or (t-BINAP)

Step A: Preparation of [(C₂H₅)₂NH₂]⁺[Ru₂Cl₅((R)-BI-NAP)₂]⁻ • CH₃Ph Structure 12

Figure 1:
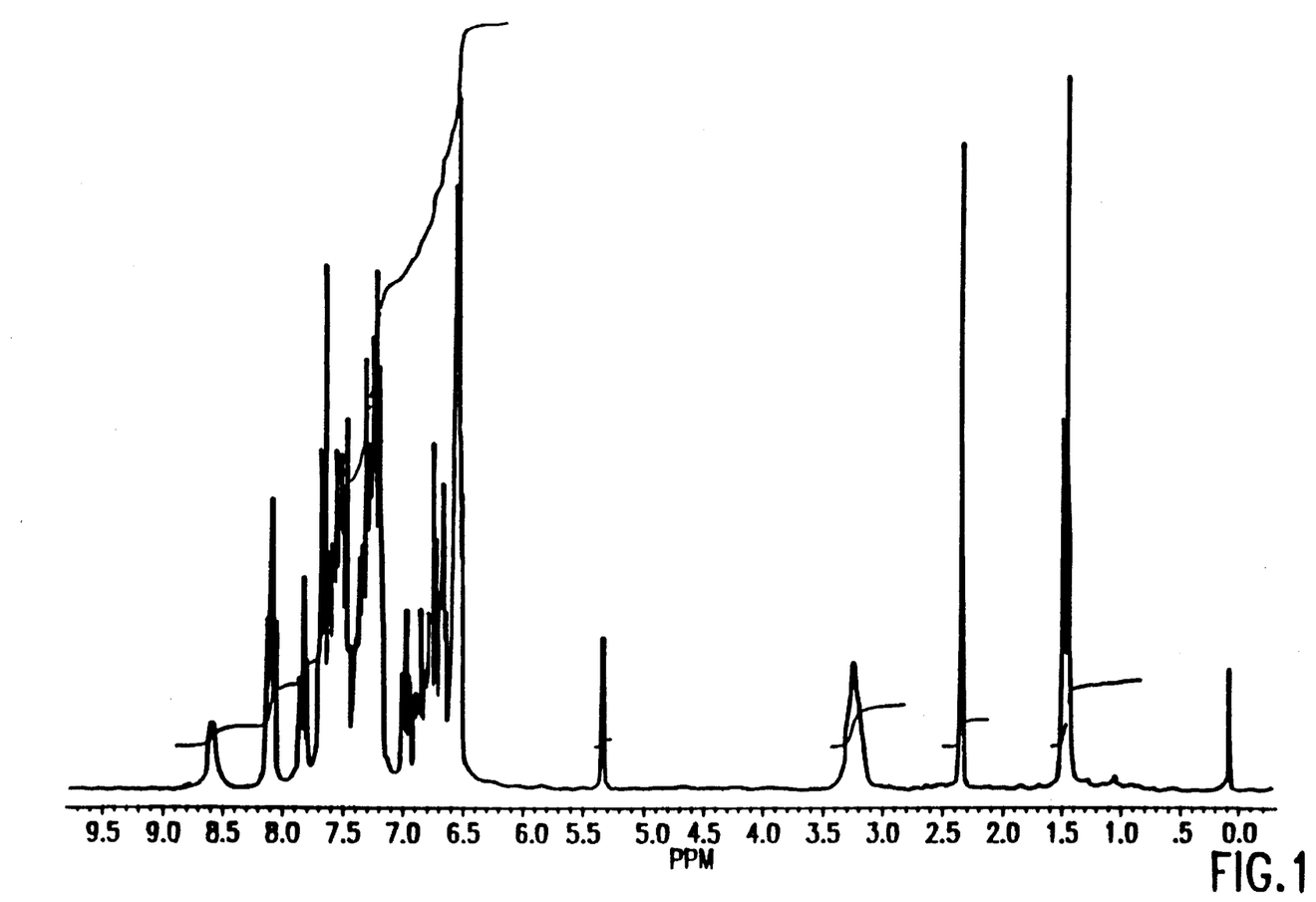
FIG. 1. 250 MHz $^1$H NMR of [(C$_2$H$_5$)$_2$NH$_2$]$^+$[Ru$_2$Cl$_5$((R)-BINAP)$_2$]$^-$•CH$_3$Ph in CD$_2$Cl$_2$ at room temperature.

(Cyclooctadienyl)ruthenium dichloride (214 mg, 0.76 mmol) and (R)-BINAP (500 mg, 0.80 mmol) were placed in a 50 mL round bottom flask and connected to a double ended filter (Kontes #215500-6044) with a 100 mL round bottom flask at the opposite end. Vacuum grease was used to ensure an air-tight seal. Rubber bands were a simple and effective way of holding the apparatus together. The entire apparatus was evacuated and filled with nitrogen. Dry toluene (17 mL) and dry triethylamine (1.7 mL), which had been deoxygenated with flowing nitrogen for several minutes, were added via the lower side arm. The vessel was sealed and the mixture heated to 140° C. producing a deep brick red colored solution. After 4 hours the apparatus was allowed to cool to room temperature with vigorous stirring while the catalyst precipitated. The apparatus was vented to nitrogen and inverted to filter the product using vacuum on the lower side arm and nitrogen on the upper. The precipitate was washed with deoxygenated toluene (17 mL), and the flask containing the filtrate was exchanged for an empty one. ($^{31}$P NMR showed that the filtrate contained none of the desired product.) The entire apparatus was put under vacuum and the product was dried overnight to give 470 mg (75%) of a dark red solid: $^1$H NMR (CD₂Cl₂, 400.13 MHz) δ 8.53(br s, 2H), 8.07 (t, J=8.8 Hz, 4H), 7.82 (t, J=8.3 Hz, 2H), 7.65 (m, 6H), 7.55 (m, 4H), 7.47 (m, 4H), 7.4–7.1 (m, 18H), 6.95 (m, 2H), 6.84 (t, J=7.4 Hz, 2H), 6.8–6.7 (om, 4H), 6.7–6.6 (om, 4H), 6.6–6.5 (ore, 12H), 3.24 (br m, 6H), 2.3 (s,3H), 1.45 (t, J=7.3 Hz, 9H) [See FIG. 1 for $^1$H NMR spectrum]; $^{31}$P NMR (CD₂Cl₂, 161.98 MHz) δ 56.5 (d, J=38.0 Hz), 52.3 (d, J=38.0 Hz); Analysis Calc'd for C₉₉H₈₄Cl₅NP₄Ru₂: C 66.39, H 4.73, N 0.78, Cl 9.90, P 6.92; Found C 66.06, H 4.74, N 0.74, Cl 9.79, P 6.91.

Figure 2A:
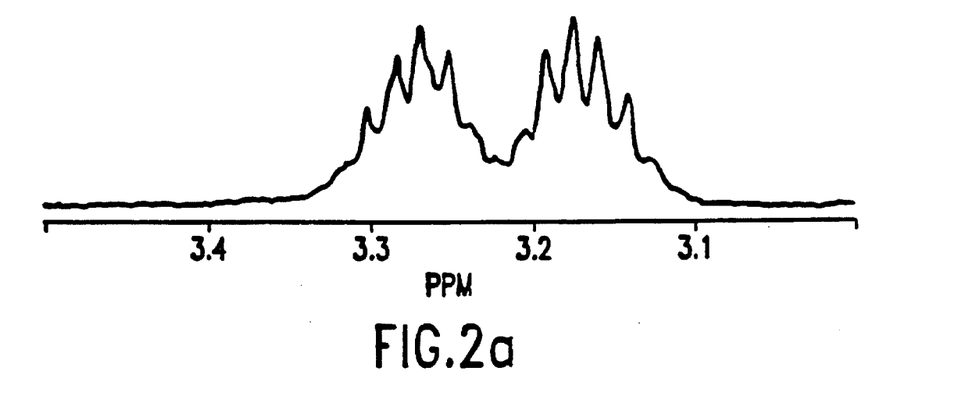
Figure 2B:
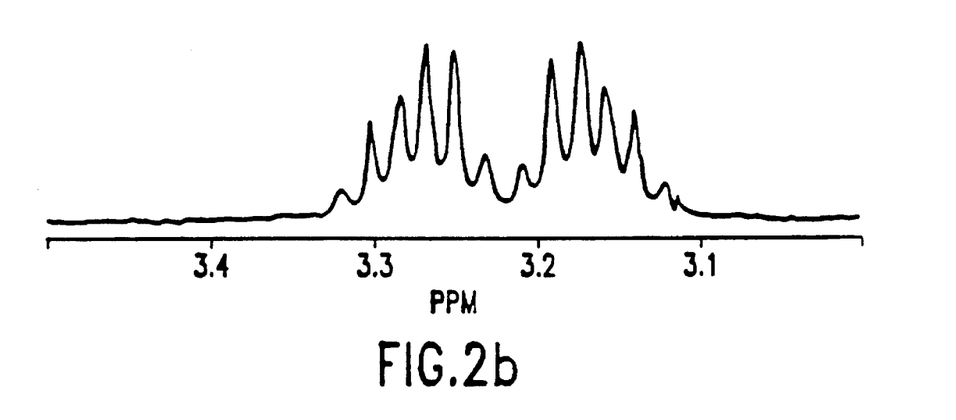
Figure 2C:
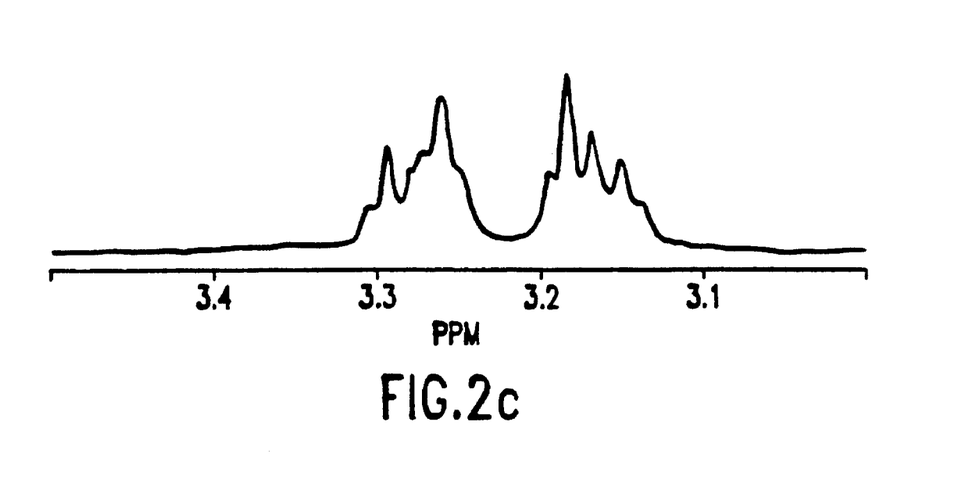

Decoupling and spiking experiments unequivocally established the presence of diethylammonium ion. At −40° C. the methylene protons of the diethylammonium appear as two multiplets at 3.2 ppm. [See FIG. 2(a) for $^1$H NMR spectrum] When the triplet at 1.4 ppm was irradiated the signal at 3.2 ppm appears as two doublets of triplets. [See FIG. 2(c) for $^1$H NMR spectrum] When the broad singlet at 8.53 ppm is irradiated the signal at 3.2 ppm appears as two doublets of quartets. [See FIG. 2(b) for $^1$H NMR spectrum]. When diethylamine was added to the solution the signal at 3.2 ppm was seen to diethylamine was added to the solution the signal at 3.2 ppm was seen to coalesce with the diethylamine signal. Triethylamine did not produce this behavior.

13

A⌒A represents:

(BINAP)

or (t-BINAP)

Step B: Preparation of Ru₂Cl₄((R)-BINAP)₂ Structure 13

The catalyst 12 (12 mg, 6.7 μmol) was loaded into a gas tight NMR robe (available from Wilmad) which was evacuated and refilled with nitrogen. Dry methylene chloride-d₂ (0.8 mL) was deoxygenated by bubbling with nitrogen for 2 minutes. It was added with a thin needle by partially unstoppering the tube while nitrogen was flowing through the plug, flushing air away from its mouth. The s atmosphere over the solvent was immediately purged by carefully evacuating and refilling with nitrogen. Catalyst dissolution was aided by the use of sonication or a vortex mixer. Methanesulfonic acid (4 μL, 62 μmol) was added to give the desired product: $^1$H NMR (CD₂Cl₂, 400.13 MHz) δ 8.14 (d, J=7.9 Hz, 2H), 8.10 (d,d, J=9.1,1.6 Hz, 2H), 7.73 (d, J=7.9 Hz, 2H), 7.65 (t, J=7.5 Hz, 2H), 7.59 (m, 2H), 7.55–7.35 (om, 22H), 7.26–7.09 (om, 18H), 6.82–6.77 (om, 4H), 6.15 (m, 4H), 6.05 (d, J=8.7 Hz, 2H), 5.83 (dd, J=12.3, 7.9 Hz, 4H); $^{31}$p NMR (CD₂Cl₂, 161.98 MHz) δ 62.6 (d, J=40.3 Hz), 13.7 (d, J =40.3 Hz ).

14

A⌒A represents:

(BINAP)

or (t-BINAP)

Step C: Preparation of [Ru₂Cl₄((R)-BINAP)₂(H₂)₂] Structure 14

A gas tight NMR tube containing 13 was put under a hydrogen atmosphere by evacuating and filling with hydrogen at a positive pressure of 8 psi. To ensure saturation of the solution, the tube was put on a vortex mixer while attached to the manifold and stirred for 10 minutes.

The $^1$H and $^{31}$P spectra indicate that the hydrogen adduct is a mixture of conformational or configurational forms. $^1$H NMR (CD₂Cl₂, 400.13 MHz) δ 8.2–5.8 (om), −9.85, −10.08, −10.2, −10.88, −11.12, −11.52; $^{31}$P NMR (CD₂Cl₂, 161.98 MHz) δ 58.8 (d, J=29.7 Hz), 56.2 (d, J=30.4 Hz), 55.1 (d, J=32.4 Hz), 54.9 (d, J=31.7 Hz), 51.7 (d, J=29.7 Hz), 50.9 (d, J=31.0 Hz), 50.5 (d, J=33.1 Hz), 48.5 (d, J=31.7 Hz), 47.2 (d, J=30.4 Hz), 46.7 (d, J=33.1 Hz), 46.4 (d, J=32.4 Hz), 44.9 (d, J=31.0 Hz).

The species 13 and 14 have been shown to be active catalysts as demonstrated in the following experiment:

To the above mixture methyl acetoacetate (20 μL) and methanol (100 μL) were added, and the NMR signals for species 14 immediately disappeared and methyl 4ohydroxybutyrate and 13 appeared. After standing over night, the hdroxy product was isolated. Examination of the (S)-Mosher ester of methyl 4-hydroxybutyrate showed the product to be >90 % enantiomeric excess.

EXAMPLE 2

[(C₂H₅)₂NH₂]⁺[Ru₂Cl₅((R)-t-BINAP)₂]⁻•toluene

To a 50 mL round bottom flask was charged 500 mg of (S)-t-BINAP 1, 197 mg of RuCl₂[COD]$_n$ polymer 2, 1.4 mL of Et₃N and 17 mL of degassed toluene. The flask was sealed and heated to 140° C. for 6 hours. The dark red homogeneous solution was cooled to ambient temperature and the solution was concentrated under reduced pressure to 8 mL. Then 12 mL of heptanes was added and the solution was stirred for one hour. The Ruthenium polymer precipitated and was filtered off via double ended filter. The homogeneous solution was concentrated under reduced pressure to 8 mL. Then 12 mL of heptanes was added and the solution was stirred for one hour. The catalyst precipated and was filtered off via doubled ended funnel (schlenk ware). The precitate was dried under vacuum, giving 300 mg of light yellow solid for 55% yield.

EXAMPLE 3

[(C₂H₅)₂NH₂]⁺[Ru₂Cl₅((R)-BINA)₂]⁻•xylene (Cyclooctadienyl)ruthenium dichloride (2.14 g, 7.6 mmol) and (R)-BINAP (5.00 g, 8.0 mmol) were placed in a 50 mL round bottom flask and connected to a double ended filter (Kontes #215500-6044) with a 1000 mL round bottom flask at the opposite end. Vacuum grease was used to ensure an air-tight seal. The entire apparatus was evacuated and filled with nitrogen. Dry xylenes (170 mL) and dry triethylamine (17 mL), which had been deoxygenated with flowing nitrogen for several minutes, were added via the lower side arm. The mixture was heated to 140 ° C. producing a deep brick red colored solution. After 4 hours the apparatus was allowed to cool to room temperature with vigorous stirring while the catalyst precipitated. The apparatus inverted to filter the product using vacuum on the lower side arm and nitrogen on the upper. The precipitate was washed with deoxygenated xylene (17 mL), and the flask containing the filtrate was exchanged for an empty one. The entire apparatus was put under vacuum and the product was dried overnight to give 440 mg (69%) of a dark red solid: $^1$H NMR (CD₂Cl₂, 400.13 MHz) δ 8.07 (t, J=8.8 Hz, 4H), 7.82 (t, J=8.3 Hz, 2H), 7.65 (m, J=8.3 Hz, 6H), 7.55 (m, 4H), 7.47 (m, 4H), 7.4–7.1 (om, 20H), 6.95 (m, 2H), 6.84 (t, J=7.4 Hz, 2H), 6.8–6.7 (om, 4H), 6.7–6.6 (om, 4H), 6.6–6.5 (om, 12H), 3.24 (m, 6H), 2.5–2.3 (3 singlets, 6H), 1.45 (t, J=7.3 Hz, 9H); 31 p NMR (CD₂Cl₂, 161.98 MHz) δ 56.5 (d, J=38.0 Hz), 52.3 (d, J=38.0 Hz).

EXAMPLE 4 t-Butyl 3-hydroxy-6-methoxy hexanoate

Step A: Preparation of t-butyl 3-keto-6-methoxy hexanoate (Ketoester 2)

The dianion of methyl acetoacetate, generated with sodium hydride and n-butyl lithium in THF at −15° C., is alkylated with 1.2 equivalents of bromoethyl methyl ether. The reaction proceeds in 6–8 hours to a level of 3 wt % residual starting material and is worked up with methyl t-butyl ether (MTBE) and saturated ammonium chloride solution. Residual methyl acetoacetate (b.p. 159° C.) is removed by flushing crude product with four to seven volumes of xylene to provide the alkylated ketoester containing <0.25 wt % methyl acetoacetate in 73–77% yield.

The methyl ester is transesterified to the t-butyl ester in 95:5-toluene:t-butanol by refluxing the solvent through 5A molecular sieves. The boiling point of the solvent mixture is 107°–111 ° C., well above the boiling point of t-butanol, which can be slowly lost from the vessel and must be replaced as needed. After concentration, the t-butyl ester is produced in 95% yield with <1% remaining methyl ester.

Step B: Preparation of t-butyl 3-hydroxy-6-methoxy hexanoate (β-hydroxyester 3)

The hydrogenation catalyst [(C₂H₅)₂NH₂]⁺[Ru₂Cl₅((R)BINAP)₂]⁻ is not commercially available and must be prepared from [RuCl₂(COD)]ₙ and (R)-BINAP (see Example 1). Twenty gram batches are conveniently prepared in a 1 L flask. Use of a double ended filter allows convenient isolation of the product on this scale. The catalyst, which can be handled and weighed in air, should be stored under nitrogen.

Asymmetric reduction of ketoester 2 is conducted in methanol at 45° C. under 1034 N/mm² (150 psi) hydrogen with 0.09 mol % (0.4 wt %) [(C₂H₅)₂NH₂]⁺[Ru₂Cl₅((R)-BINAP)₂]⁻. The reaction mixture should be deoxygenated with nitrogen and the vessel thoroughly evacuated and flushed with nitrogen prior to pressurization with hydrogen. The reaction is exothermic and requires periodic cooling to maintain the temperature at 45°. After 4 hours hydrogen uptake is complete and the catalyst is precipitated with hexane and filtered away. Concentration provides a >97% yield of the alcohol whose enantiomeric excess is determined to be 97% by proton NMR analysis of the derived Mosher ester.

The hydrogenation reaction is very susceptible to the presence of basic impurities and acidification of these with small amounts of strong acid is required.

Transesterification during the reaction can result from either high temperatures or the presence of excess amounts of acid. Thus, the reaction temperature should be kept at 45° and the minimum possible amount of HCl should be used.

EXAMPLE 5 tert-Butyl 3(R)-hydroxybutyrate tert-Butyl acetoacetate [15] (14.5 g, 90 mmol) and methanol (30 mL) were mixed and deoxygenated with flowing nitrogen for 5 minutes in a septum covered Parr shaker bottle. The catalyst prepared as described above (36 mg, 0.02 mmol) was added along with 2N HCl (0.041 mL, 0.082 mmol). The mixture was transferred to a standard Parr shaker apparatus and flushed by evacuating and refilling with nitrogen and then hydrogen several times. The apparatus was heated at 40° C. with shaking under 50 psi of hydrogen. After 20 min the reaction became a homogeneous clear yellow solution which took up hydrogen for approximately eight hours. At this time the reaction was complete and the mixture was cooled and diluted with hexane (30 mL) to precipitate the catalyst, which was filtered away. The filtrate was concentrated to give tert-butyl 3(R)-hydroxybutyrate [16] (14.5 g, 97%).

EXAMPLE 6 tert-Butyl 3(R)-hydroxybutyrate

Following the procedure described in Example 3 with the exception that 2N H₂SO₄ was substituted for the 2N HCl ten-butyl acetoacetate was reduced to the titled product.

EXAMPLE 7

17
MW 272.31

18
MW 274.31

In a 25 mL round bottom flask with a septum the p-keto amide 17 (1 g) was dissolved in methanol (4 mL). The solution was deoxygenated with nitrogen for 20 minutes and then the finely ground $[(C_2H_5)_2NH_2]^+[Ru_2Cl_5((S)\text{-BINAP})_2]^-$ catalyst (15.5 mg) (prepared as described in Example 1 ) was added. The solution was degassed with nitrogen for 5 minutes and 2N hydrochloric acid (0.092 mL) was added. The mixture was cannulated into the reaction pressure vessel. The apparatus was heated at 60° C. with shaking under 40 psi of hydrogen for 20 hours.

After 20 h the reaction mixture was removed from the reaction pressure vessel. The vessel was rinsed with methanol (3 mL) which was combined with the reaction mixture. The solution was concentrated under reduced pressure to an off-white solid.

The crude reaction mixture gave a 87:13 ratio of the R:S hydroxy esters.

The yield was 100%.

EXAMPLE 8

19
MW 208.65

20
MW 210.65

In a 25 mL round bottom flask with a septum the p-keto amide HCL salt 19 (1 g) was dissolved in methanol (16 mL). The solution was deoxygenated with nitrogen for 20 minutes and then the finely ground $[(C_2H_5)_2NH_2]^+[Ru_2Cl_5((S)\text{-BINAP})_2]^-$ catalyst (20.2 mg) (prepared as described in Example 1 ) was added. The solution was degassed with nitrogen for 5 minutes and 2N hydrochloric acid (0.120 mL) was added. The mixture was cannulated into the reaction pressure vessel. The apparatus was heated at 60° C. with shaking under 40 psi of hydrogen for 20 hours.

After 20 h the reaction mixture was removed from the reaction pressure vessel. The vessel was rinsed with methanol (3 mL) which was combined with the reaction mixture. The solution was concentrated under reduced pressure to an off-white solid. The crude reaction mixture gave a 97:3 ratio of the R:S hydroxy amides.

The yield was 80%.

EXAMPLE 9

21
MW 363.40

22
MW 265.40

In a 25 mL round bottom flask with a septum the β-keto amide mesylate 21 (0.957 g) was dissolved in methanol (2.5 mL). The solution was deoxygenated with nitrogen for 20 minutes and then the finely ground $[(C_2H_5)_2NH_2]^+[Ru_2Cl_5((S)\text{-BINAP})_2]^-$ catalyst (11 mg) (prepared as described in Example 1 ) was added. The solution was degassed with nitrogen for 5 minutes and 2N hydrochloric acid (0.020 mL) was added. The mixture was cannulated into the reaction pressure vessel. The apparatus was heated at 40° C. with stirring under 150 psi of hydrogen for 20 hours.

After 20 h the reaction mixture was removed from the reaction pressure vessel. The vessel was rinsed with methanol (3 mL) which was combined with the reaction mixture. The solution was concentrated under reduced pressure to an off-white solid. The crude reaction mixture gave a 91:9 ratio of the R:S hydroxy amide mesylates. The yield was 80%.

EXAMPLE 10

(R)-Trans-2-Methoxycarbonylcyclopentanol

2-Methoxycarbonyl-cyclopentanone (4.26 g) was dissolved in methanol (5 mL) and 0.1 mL 1N HCl was added. The mixture was deoxygenated, 1 (36 mg) was added and the mixture was exposed to hydrogen at 40 psi and 40° in a Parr shaker apparatus. After 6 h the reaction was complete, providing a single product (4.10 g) in >95% ee: $^1$H NMR (CDCl$_3$, 250 MHz) 4.40 (q, J=7.5 Hz, 1H), 3.71 (s, 3H), 2.65 (q, J=7.2 Hz, 1H), 2.1–1.5 (m, 6H).

EXAMPLE 11

Methyl 3-Hydroxy-2-methylbutyrate

Methyl 2-methylacetoacetate was hydrogenated under the conditions set forth in Example 2 or 3, to give a 6:4 mixture of trans:cis product. Enantiomeric excess of the major isomer was >97%.

EXAMPLE 12

Methyl 5-(R)-hydroxyvalerate

A mixture of methyl levulinate (10.0 g, 77 mmol), methanol (10 mL) and concentrated HCl (0.4 mL) was deoxygenated with bubbling nitrogen for 2 minutes. [(C$_2$H$_5$)$_2$NH$_2$]$^+$ [Ru$_2$Cl$_5$ ((R)-BINAP)$_2$]$^-$ (50 mg) was added and the mixture placed in a standard Parr shaker apparatus. After evacuating and flushing with nitrogen three times, the mixture was evacuated and exposed to 40 psi hydrogen pressure at 40° C. for 48 h. The solvent was removed in vacuo to give the product (9.90 g, 99% yield) which was identical to a commercially available (Aldrich) racemic sample by $^1$H NMR. The optical purity was shown to be 99:1 by obtaining proton NMR spectrum of the product (1 mL) and (S)-(+)-2,2,2-trifluro-1-(9-anthryl)ethanol (27 mg) in CDCl$_3$. Peak assignments were made by spiking with a sample of the racemate. Methyl 5-(R)ohydroxyvalerate spontaneously lactonizes to give 5-(R)-γ-valerolactone.

EXAMPLE 13

Ethyl 3-hydroxybutyrate

This was prepared from ethyl acetoacetate in ethanol according to the procedure of Example 4 or 5. Enantiomeric excess was measured to be 97%. $^1$H NMR (CDCl$_3$, 250 MHz) 4.20 (m, 1H), 4.10 (q, J=7.5 Hz, 1H), 2.51 (m, 2H), 1.2 (m, 5H).

What is claimed is:

1. A process for the asymmetric reduction of a β or γ-ketoester or β or γ-ketoamide of structural formula:

to form a β or γ-hydroxyester or β or γ-hydroxyamide of formula I:

wherein:

$R^1$ is straight or branched C$_1$–C$_4$ alkyl;

X is O or NR$^5$;

Y is C(R$^2$)$_2$ or a single bond;

$R^2$ is: H, or straight or branched C$_1$–C$_6$ alkyl;

$R^3$ is: H, straight or branched C$_1$–C$_6$ alkyl, CH$_2$NHCOR$^6$, or $R^1$ and $R^3$ taken together form a 5 to 7 membered lactone or lactam;

$R^4$ is:

CH$_3$, (a)

CH$_2$Cl, (b)

(c)

(d)

(e)

(f)

(g)

(h)

(i)

(j)

-continued
or

CH₂CH₂CH₂OCH₃;  (k)

R³ and R⁴ taken together form a ring of 5 to 7 carbons, in which R³ and R⁴ represent a carbon chain of 3 to 5 carbons;

R⁵ is H, straight or branched $C_1$–$C_4$ alkyl, or $CO_2$ $C_1$–$C_4$ alkyl; and R⁶ is straight or branched $C_1$–$C_4$ alkyl, or O-$C_1$–$C_4$ alkyl, phenyl, O-benzyl;

which comprises treating the β- or γ-ketoester or β- or γ-ketoamide in a $C_1$–$C_3$ alkanol with a Ru(II)-arBINAP derived catalyst, $(C_2H_5)_2NH_2^+[Ru_2Cl_5(2,2'$-bis (diarylphosphino)-1,1'-binaphthyl)$_2]^-$, wherein aryl is defined as phenyl, o-, m-, and p-tolyl, in the presence of a strong acid selected from the group consisting of: HCl, $H_2SO_4$, $H_3PO_4$, $CH_3SO_3H$, at about a concentration of between 0.1 to 10 mole %, at a temperature of about 40°–50° C. and about 50 to 1400 N/mm² of hydrogen.

2. The process of claim 1 wherein the Ru(II)-BINAP derived catalyst is $[(C_2H_5)_2NH_2]^+[Ru_2Cl_5(BINAP)_2]^-$•solvate.

3. The process of claim 2 wherein the solvate is selected from the group consisting of benzene, toluene, xylene, chlorobenzene, or 1,2-, 1,3-,or 1,4-dichlorobenzene.

4. The process of claim 3 wherein $C_{1-3}$ alkanol is methanol.

5. The process of claim 4 wherein the concentration of the β-ketoester in the reaction mixture is about 0.5 to 2.25 molar.

6. The process of claim 5 wherein the amount of catalyst is about 0.02 to 0.1 mole %.

7. The process of claim 6 wherein the strong acid is selected from the group consisting of HCl, $H_2SO_4$, or $CH_3SO_4$.

8. The process of claim 7 wherein the concentration of the strong acid is about 0.1 to 10 mole %.

9. The process of claim 8, wherein the strong acid is HCl.

10. The process of claim 1 for the asymmetric reduction of a β-ketoester or β-ketoamide of structural formula:

to form the β-hydroxyester or β-hydroxyamide of formula:

wherein:

R¹ is straight or branched $C_1$–$C_4$ alkyl;

X is O or NR⁵;

R² is: H, or straight or branched $C_1$–$C_6$ alkyl;

R³ is: H, straight or branched $C_1$–$C_6$ alkyl, $CH_2NHCOR^6$, or R¹ and R³ taken together form a 5 to 7 membered lactone or lactam;

R⁴ is:

CH₃,  (a)

CH₂Cl,  (b)

(c)

(d)

(e)

(f)

(g)

(h)

(i)

(j)

or

CH₂CH₂CH₂OCH₃;  (k)

R³ and R⁴ taken together form a ring of 5 to 7 carbons, in which R³ and R⁴ represent a carbon chain of 3 to 5 carbons;

R⁵ is H, straight or branched $C_1$–$C_4$ alkyl, or $CO_2$ $C_1$–$C_4$ alkyl; and

R⁶ is straight or branched $C_1$–$C_4$ alkyl, or O-$C_1$–$C_4$ alkyl, phenyl, O-benzyl;

which comprises treating the β-ketoester in a $C_1$–$C_3$ alkanol with a Ru(II)-arBINAP derived catalyst, $(C_2H_5)_2NH_2^+$ $[Ru_2Cl_5(2,2'$-bis(diarylphosphino)- 1,1'-binaphthyl)$_2]^-$, wherein aryl is defined as phenyl, o-, m-, and p-tolyl, in the presence of a strong acid selected from the group consisting of: HCl, $H_2SO_4$, $H_3PO_4$, $CH_3SO_3H$, at about a concentration of between 0.1 to 10 mole %, at a temperature of about 40°–50° C., and about 50 to 1400 N/mm² of hydrogen.

11. The process of claim 8 wherein the asymmetric reduction of a β-ketoester of structural formula:

to form the β-hydroxyester of formula:

wherein:

$R^1$ is straight or branched $C_1$–$C_4$ alkyl;

$R^2$ and $R^3$ are: H;

$R^4$ is:

CH$_3$, (a)

CH$_2$Cl, (b)

(c)

(d)

(e)

(f)

(g)

(h)

(i)

(j)

or

CH$_2$CH$_2$CH$_2$OCH$_3$; (k)

$R^3$ and $R^4$ taken together form a ring of 5 to 7 carbons, in which $R^3$ and $R^4$ represent a carbon chain of 3 to 5 carbons; and

$R^5$ is H, straight or branched $C_1$–$C_4$ alkyl, or CO$_2$ $C_1$–$C_4$ alkyl;

which comprises treating the β-ketoester in a $C_1$–$C_3$ alkanol with a Ru(II)-BINAP derived catalyst, $(C_2H_5)_2NH_2^+$ [Ru$_2$Cl$_5$(2,2'-bis(diarylphosphino)-1,1'-binaphthyl)$_2$]$^-$, wherein aryl is defined as phenyl, o-, m-, and p-tolyl, in the presence of a strong acid selected from the group consisting of: HCl, H$_2$SO$_4$, H$_3$PO$_4$, CH$_3$SO$_3$H, at about a concentration of between 0.1 to 10 mole %, at a temperature of about 40°–50° C., and about 50 to 1400 N/mm$^2$ of hydrogen.

12. The process of claim 9 for the asymmetric reduction of a β-ketoester of structural formula:

to form the β-hydroxyester of formula:

wherein:

$R^1$ is methyl, ethyl or t-butyl; and $R^2$ and $R^3$ are: H;

$R^4$ is CH$_3$, CH$_2$CH$_2$CH$_3$, CH$_2$CH$_2$CH$_2$OCH$_3$, or $R^3$ and $R^4$ taken together form a ring of 5 carbons, in which $R^3$ and $R^4$ represent a carbon chain of 3 carbons;

which comprises treating the β-ketoester in a $C_1$–$C_3$ alkanol with a Ru(II)-arBINAP derived catalyst, $(C_2H_5)_2NH_2^+$ [Ru$_2$Cl$_5$(2,2'-bis(diarylphosphino)-1,1'-binaphthyl)$_2$]$^-$, wherein aryl is defined as phenyl, o-, m-, and p-tolyl, in the presence of a strong acid selected from the group consisting of: HCl, H$_2$SO$_4$, H$_3$PO$_4$, CH$_3$SO$_3$H, at about a concentration of between 0.1 to 10 mole %, at a temperature of about 40°–50° C., and about 50 to 1400 N/mm$^2$ of hydrogen.

13. The process of claim 8 wherein the asymmetric reduction of a β-ketoamide of structural formula:

to form the β-hydroxyamide of formula:

wherein:

$R^1$ is straight or branched $C_1$–$C_4$ alkyl;

$R^2$ and $R^3$ are: H;

$R^4$ is:

CH$_3$, (a)

CH$_2$Cl, (b)

-continued

(c)

(d)

(e)

(f)

(g)

(h)

(i)

(j)

or

$CH_2CH_2CH_2OCH_3$; (k)

$R^3$ and $R^4$ taken together form a ring of 5 to 7 carbons, in which $R^3$ and $R^4$ represent a carbon chain of 3 to 5 carbons; and

$R^5$ is H, straight or branched $C_1$–$C_4$ alkyl, or $CO_2$ $C_1$–$C_4$ alkyl;

which comprises treating the β-ketoamide in a $C_1$–$C_3$ alkanol with a Ru(II)-arBINAP derived catalyst, $(C_2H_5)_2NH_2^+[Ru_2Cl_5(2,2'-bis(diarylphosphino)-1,1'-binaphthyl)2]^-$, wherein aryl is defined as phenyl, o-, m-, and p-tolyl, in the presence of a strong acid selected from the group consisting of: HCl, $H_2SO_4$, $H_3PO_4$, $CH_3SO_3H$, at about a concentration of between 0.1 to 10 mole %, at a temperature of about 40°–50° C., and about 50 to 1400 N/mm² of hydrogen.

14. The process of claim 9 for the asymmetric reduction of a β-ketoamide of structural formula:

to form the β-hydroxyamide of formula:

wherein:

$R^1$ is methyl, ethyl or t-butyl; and

$R^2$ and $R^3$ are: H;

$R^4$ is:

which comprises treating the β-ketoamide in a $C_1$–$C_3$ alkanol with a Ru(II)-arBINAP derived catalyst, $(C_2H_5)_2NH_2^+[Ru_2Cl_5(2,2'-bis(diarylphosphino)-1,1'-binaphthyl)_2]^-$, wherein aryl is defined as phenyl, o-, m-, and p-tolyl, in the presence of a strong acid selected from the group consisting of: HCl, $H_2SO_4$, $H_3PO_4$, $CH_3SO_3H$, at about a concentration of between 0.1 to 10 mole %, at a temperature of about 40°–50° C., and about 50 to 1400 N/mm² of hydrogen.

15. In a process for the asymmetric reduction of a β or γ-ketoester or β or γ-ketoamide of structural formula:

to form a β or γ-hydroxyester or β or γ-hydroxyamide of formula I:

I in the presence of a Ru(II)-arBINAP derived catalyst, $(C_2H_5)_2NH_2^+[Ru_2\quad Cl_5(2,2'-bis(diarylphosphino)-1,1'-binaphthyl)_2]^-$, wherein aryl is defined as phenyl, o-, m-, and p-tolyl, at elevated temperature and pressure, wherein:

$R^1$ is straight or branched $C_1$–$C_4$ alkyl;

X is O or $NR^5$;

Y is $C(R^2)_2$ or a single bond;

$R^2$ is: H, or straight or branched $C_1$–$C_6$ alkyl;

$R^3$ is: H, straight or branched $C_1$–$C_6$ alkyl, $CH_2NHCOR^6$, or $R^1$ and $R^3$ taken together form a 5 to 7 membered lactone or lactam;

$R^4$ is:

$CH_3$, (a)

$CH_2Cl$, (b)

(c)

(d) -CHCH₂-⟨phenyl⟩, NHBoc (e) -CH-CH₂-⟨cyclohexyl⟩, NHBoc (f) -CHCH₂-CH(CH₃)₂, NHBoc (g) pyrrolidine with OMs, N-Boc, H (h) pyrrolidine with OH, N-Boc, H (i) pyrrolidine with OH, N-H, H (j) -CH₂-CH=CH-CH₃, or (k) CH₂CH₂CH₂OCH₃;

$R^3$ and $R^4$ taken together form a ring of 5 to 7 carbons, in which $R^3$ and $R^4$ represent a carbon chain of 3 to 5 carbons;

$R^5$ is H, straight or branched $C_1$–$C_4$ alkyl, or $CO_2$ $C_1$–$C_4$ alkyl; and

$R^6$ is straight or branched $C_1$–$C_4$ alkyl, or O-$C_1$–$C_4$ alkyl, phenyl, O-benzyl;

and the improvement comprises conducting the reduction at about 40°–50° C. and about 50 to 1400 N/mm² of hydrogen, in the presence of a strong acid selected from the group consisting of: HCl, H₂SO₄, H₃PO₄, CH₃SO₃H, at about a concentration of between 0.1 to 10 mole %.

16. In a process for the asymmetric reduction of a β or γ-ketoester or β or γ-ketoamide of structural formula:

to form the β-hydroxyester or β-hydroxyamide of formula:

in the presence of a Ru(II)-arBINAP derived catalyst, $(C_2H_5)_2NH_2^+[Ru_2Cl_5(2,2'$-bis(diarylphosphino)-1,1'-binaphthyl)$_2]^-$, wherein aryl is defined as phenyl, o-, m-, and p-tolyl, at elevated temperature and pressure, wherein:

$R^1$ is straight or branched $C_1$–$C_4$ alkyl;

X is O or $NR^5$;

$R^2$ is: H, or straight or branched $C_1$–$C_6$ alkyl;

$R^3$ is: H, straight or branched $C_1$–$C_6$ alkyl, $CH_2NHCOR^6$, or $R^1$ and $R^3$ taken together form a 5 to 7 membered lactone or lactam;

$R^4$ is:

(a) CH₃, (b) CH₂Cl, (c) CH₂OCH₂-⟨phenyl⟩-OCH₃, (d) -CHCH₂-⟨phenyl⟩, NHBoc (e) -CH-CH₂-⟨cyclohexyl⟩, NHBoc (f) -CHCH₂-CH(CH₃)₂, NHBoc (g) pyrrolidine with OMs, N-Boc, H (h) pyrrolidine with OH, N-Boc, H (i) pyrrolidine with OH, N-H, H (j) -CH₂-CH=CH-CH₃, or (k) CH₂CH₂CH₂OCH₃;

$R^3$ and $R^4$ taken together form a ring of 5 to 7 carbons, in which $R^3$ and $R^4$ represent a carbon chain of 3 to 5 carbons;

$R^5$ is H, straight or branched $C_1$–$C_4$ alkyl, or $CO_2$ $C_1$–$C_4$ alkyl; and R6 is straight or branched $C_1$–$C_4$ alkyl, or O-$C_1$–$C_4$ alkyl, phenyl, O-benzyl;

and the improvement comprises conducting the reduction at about 40°–50° C. and about 50 to 1400 N/mm² of hydrogen, in the presence of a strong acid selected from the group consisting of: HCl, $H_2SO_4$, $H_3PO_4$, $CH_3SO_3H$, at about a concentration of between 0.1 to 10 mole %.

17. In a process for the asymmetric reduction a β-ketoester of structural formula:

to form the β-hydroxyester of formula:

in the presence of a Ru(II)-arBINAP derived catalyst, $(C_2H_5)_2NH_2^+$ $[Ru_2Cl_5(2,2'\text{-bis(diarylphosphino)-}1,1'\text{-binaphthyl})_2]^-$, wherein aryl is defined as phenyl, o-, m-, and p-tolyl, at elevated temperature and pressure, wherein:

$R^1$ is methyl, ethyl or t-butyl; and $R^2$ and $R^3$ are: H;

$R^4$ is $CH_3$, $CH_2CH_2CH_3$, $CH_2CH_2CH_2OCH_3$, or $R^3$ and $R^4$ taken together form a ring of 5 carbons, in which $R^3$ and $R^4$ represent a carbon chain of 3 carbons;

and the improvement comprises conducting the reduction at about 40°–50° C. and about 50 to 1400 N/mm² of hydrogen, in the presence of a strong acid selected from the group consisting of: HCl, $H_2SO_4$, $H_3PO_4$, $CH_3SO_3H$, at about a concentration of between 0.1 to 10 mole %.

18. In a process for the asymmetric reduction of a β-ketoamide of structural formula:

to form the β-hydroxyamide of formula:

in the presence of a Ru(II)-arBINAP derived catalyst, $(C_2H_5)_2NH_2^+$ $[Ru_2Cl_5(2,2'\text{-bis(diarylphosphino)-}1,1'\text{-binaphthyl})_2]^-$, wherein aryl is defined as phenyl, o-, m-, and p-tolyl, at elevated temperature and pressure, wherein:

$R^1$ is methyl, ethyl or t-butyl; and $R^2$ and $R^3$ are: H;

$R^4$ is:

and the improvement comprises conducting the reduction at about 40°–50° C. and about 50 to 1400 N/mm² of hydrogen, in the presence of a strong acid selected from the group consisting of: HCl, $H_2SO_4$, $H_3PO_4$, $CH_3SO_3H$, at about a concentration of between 0.1 to 10 mole %.

* * * * *

UNITED STATES PATENT AND TRADEMARK OFFICE
CERTIFICATE OF CORRECTION

PATENT NO.    : 5,508,435
DATED         : April 16, 1996
INVENTOR(S)   : Armstrong, III, et al It is certified that error appears in the above-identified patent and that said Letters Patent is hereby corrected as shown below:

On the title page, item [75] Inventors: should read -- Joseph D. Armstrong, III Jennifer L. Keller, Steven A. King, Andrew S. Thompson and Thomas R. Verhoeven --

Signed and Sealed this

Sixteenth Day of July, 1996

Attest:

BRUCE LEHMAN

*Attesting Officer*   *Commissioner of Patents and Trademarks*